United States Patent [19]

Watanabe et al.

[11] Patent Number: 5,569,784
[45] Date of Patent: Oct. 29, 1996

[54] SULFONIUM SALT AND RESIST COMPOSITION

[75] Inventors: Satoshi Watanabe; Junji Shimada; Youichi Ohsawa; Katsuya Takemura; Toshinobu Ishihara; Kazumasa Maruyama, all of Niigata-ken, Japan

[73] Assignee: Shin-Etsu Chemical Co., Ltd., Tokyo, Japan

[21] Appl. No.: 379,987

[22] Filed: Jan. 27, 1995

[30] Foreign Application Priority Data

Jan. 28, 1994 [JP] Japan .................................. 6-026170

[51] Int. Cl.$^6$ ................................................. C07C 217/48
[52] U.S. Cl. ........................ 564/430; 430/270.1; 522/31; 548/556; 548/570
[58] Field of Search .............................. 564/430; 522/31; 430/270.1; 548/556, 570

[56] References Cited

FOREIGN PATENT DOCUMENTS

A0410250  1/1991  European Pat. Off. .

OTHER PUBLICATIONS

European Search Report dated Jun. 28, 1995.
A. Michaelis, et al., Berichte der Deutschen Chemischen Gesellschaft, vol. 24, pp. 757–764 (1891).

Primary Examiner—Brian M. Burn
Attorney, Agent, or Firm—Millen, White, Zelano & Branigan, P.C.

[57] ABSTRACT

A novel sulfonium salt having at least one substituted aromatic group having acid labile groups and at least one nitrogenous aromatic group is provided. A chemically amplified, positive resist composition comprising the sulfonium salt as well as an alkali soluble resin and a dissolution inhibitor in an organic solvent has solved the PED problem.

24 Claims, No Drawings

SULFONIUM SALT AND RESIST COMPOSITION

BACKGROUND OF THE INVENTION

1. Field of the Invention

This invention relates to a novel sulfonium salt suitable for use in a chemically amplified, positive resist composition. It also relates to a chemically amplified, positive resist composition which is highly sensitive to high energy radiation such as deep-ultraviolet lights, electron rays and X-rays, can be developed with alkaline aqueous solution to form a pattern, and is thus suitable for use in a fine patterning technique.

2. Prior Art

As the LSI technology tends toward higher integration and higher speed, further refinement of pattern rules is required. The current patterning technology mostly relies on light exposure which is now approaching to the essential limit of resolution which is dictated by the wavelength of a light source. It is generally recognized that in light exposure using g-line (wavelength 436 nm) or i-line (wavelength 365 nm) as a light source, a pattern rule of about 0.5 μm is the limit. For LSIs fabricated by such light exposure technique, a degree of integration equivalent to 16 mega-bit DRAM is the limit. At present, LSIs fabricated in the laboratory have reached this stage. It is urgently required to develop a finer patterning technique.

Under such circumstances, deep-ultraviolet lithography is regarded promising as the next generation of fine patterning technology. The deep-UV lithography is capable of working on the order of 0.3 to 0.4 μm. If a less light absorbing resist is used, it is possible to form a pattern having a side wall perpendicular to the substrate. Great attention is now paid to the technique of utilizing a high illuminance KrF excimer laser as a deep-UV light source. In order to employ this technique on a mass production scale, a resist material having low light absorption and high sensitivity is desired.

From this point of view, a number of chemically amplified, positive working resist materials were recently developed using acid catalysts as disclosed in JP-B 27660/1990, JP-A 27829/1988, U.S. Pat. Nos. 4,491,628 and 5,310,619. These materials have high sensitivity, resolution and dry etching resistance and are promising as resist materials especially suited for deep-UV lithography.

Prior art chemically amplified, positive resists, however, suffer from the problem known as post-exposure delay (PED) that when deep-UV, electron beam or X-ray lithography is carried out, line patterns would have a T-top configuration, that is, patterns become thick at the top if the leave-to-stand time from exposure to post-exposure baking (PEB) is extended. This problem, which arises probably because the resist surface is reduced in solubility, becomes a serious drawback on practical application. This not only makes difficult dimensional control in the lithographic process, but also adversely affects dimensional control in the processing of substrates using dry etching. In this regard, reference is made to W. Hinsberg et al., J. Photopolym. Sci. Technol., 6 (4), 535–546 (1993) and T. Kumada et al., J. Photopolym., Sci. technol., 6 (4), 571–574 (1993). There are available no chemically amplified, positive resists which can resolve this problem and are thus practically acceptable.

It is understood that basic compounds in the air largely participate in the PED problem associated with chemically amplified, positive resists. Light exposure generates acids at the resist surface which react with basic compounds in the air and are thereby deactivated. As the leave-to-stand time until PEB is extended, more amounts of acids are deactivated and accordingly, decomposition of acid unstable groups are more unlikely to occur. As a consequence, an insolubilized layer is formed at the resist surface, resulting in a T-top configurated pattern.

It is known from JP-A 127369/1993 that the problem of resist scum can be overcome by adding a minor amount of a basic compound to chemically amplified, positive resist. Although light contrast of a mask pattern is reduced in proximity to the resolution limit, the acid concentration distribution at the mask edge can be made sharp whereby dimensional control is improved. Acids generated in masked areas by light interference are entirely neutralized by the basic compound.

It is also known from JP-A 232706/1993 and 249683/1993 that since addition of a basic compound suppresses the influence of basic compounds in the air, it is also effective for resolving the PED problem. However, the basic compound used therein is little taken into the resist film due to volatilization, less compatible with resist components, and unevenly dispersible in a resist film over its width. Thus the basic compound cannot achieve its advantages in a reproducible manner and causes a drop of resolving power.

SUMMARY OF THE INVENTION

Therefore, an object of the present invention is to provide a novel sulfonium salt suitable as a component of a chemically amplified, positive resist composition which has overcome the problem of an insoluble surface layer causing a T-top configuration, that is, the PED problem and which is suited for a fine patterning technique. Another object of the invention is to provide a chemically amplified, positive resist composition containing such a sulfonium salt.

We have found that a novel sulfonium salt having a nitrogenous aromatic group as represented by the general formula (1) shown below can be prepared, for example, by reacting a sulfoxide compound of the general formula (3) shown below with (trimethylsilyl)trifluoro-methanesulfonate, simply referred to as trimethylsilyltriflate, and an aryl Grignard reagent of the following general formula (4) shown below.

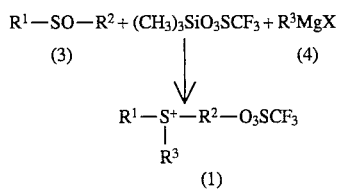

In the formulae, $R^1$, $R^2$, and $R^3$ are independently substituted or unsubstituted aromatic groups, at least one of $R^1$, $R^2$, and $R^3$ is a substituted aromatic group having acid labile groups, and at least one of the remaining R groups is a nitrogenous aromatic group. Or, all of $R^1$, $R^2$ and $R^3$ are nitrogenous aromatic group. When this sulfonium salt is used as a component of a chemically amplified, positive resist composition, the salt is effective for solving the problem of an insoluble surface layer causing a T-top configuration, that is, the PED problem and accordingly, the composition is amenable to a fine patterning technique. The composition is most effective when combined with deep-UV lithography.

Accordingly, the present invention in a first aspect provides a sulfonium salt of general formula (1).

In a second aspect, the present invention provides a chemically amplified, positive resist composition comprising the sulfonium salt. In one preferred embodiment, a chemically amplified, positive resist composition includes (A) an organic solvent, (B) an alkali soluble resin, (C) a dissolution inhibitor having acid labile groups, and (D) a sulfonium salt of formula (1). In another preferred embodiment, the composition further includes (E) a photo-acid-generator.

The resist composition containing a sulfonium salt of formula (1) has the following advantages. Since a nitrogenous substituent in the sulfonium salt of formula (1) is effective for minimizing the influence of deactivation of acid at the resist surface by basic compounds in the air, formation of a surface insoluble layer is suppressed. Since a nitrogenous substituent which is a basic group is attached to the sulfonium salt serving as a photo-acid-generator, the sulfonium salt is well compatible with the other components of the resist and thus uniformly dispersible in a resist film so that the advantages are achieved in a reproducible manner. An acid labile group in the sulfonium salt is effective for enhancing contrast. Then the sulfonium salt is suitable as a component of a chemically amplified, positive resist composition for solving the problem of an insoluble surface layer causing a T-top configuration, that is, the PED problem and thus rendering the composition amenable to a fine patterning technique.

DETAILED DESCRIPTION OF THE INVENTION

According to the present invention, a novel sulfonium salt has the general formula (1).

In formula (1), $R^1$, $R^2$, and $R^3$ are independently substituted or unsubstituted aromatic groups At least one of $R^1$, $R^2$, and $R^3$ is a substituted aromatic group having acid labile groups and at least one of the remaining R groups is a nitrogenous or nitrogen-containing aromatic group. Or, all of $R^1$, $R^2$ and $R^3$ are nitrogenous or nitrogen-containing aromatic group. The unsubstituted aromatic group is typified by a phenyl group and the substituted aromatic group having acid labile groups is typified by a tert-butoxyphenyl group. Examples of the nitrogenous aromatic group include dialkylaminophenyl groups wherein the alkyl moiety has 1 to 8 carbon atoms, a picolyloxyphenyl group and a pyridinyl group, with dimethylaminophenyl, diethylamino-phenyl, picolyloxyphenyl, and pyridinyl groups being preferred.

Several illustrative, non-limiting examples of the sulfonium salt of formula (1) include trifluoromethanesulfonic acid bis(p-tert-butoxyphenyl) (p-dimethylamino-phenyl)sulfonium, trifluoromethanesulfonic acid (p-tert-butoxypheny) bis(p-dimethylamino-phenyl)sulfonium, trifluoromethanesulfonic acid bis(p-tert-butoxyphenyl)(p-picolyloxy-phenyl) sulfonium, trifluoromethanesulfonic acid (p-tert-butoxyphenyl)bis(p-picolyloxy phenyl)sulfonium, trifluoromethanesulfonic acid (p-tert-butoxyphenyl)(p-dimethylamino-phenyl)phenylsulfonium, trifluoromethanesulfonic acid (p-tert-butoxyphenyl)(p-picolyloxy-phenyl)phenylsulfonium, trifluoromethanesulfonic acid bis(p-tert-butoxyphenyl)(pyridin-4-yl)sulfonium, trifluoromethanesulfonic acid bis(p-tert-butoxyphenyl)(pyridin-3-yl)sulfonium,trifluoromethanesulfonic acid bis(p-tert-butoxyphenyl)(pyridin-2-yl)sulfonium, trifluoromethanesulfonic acid tris(4-dimethylaminophenyl)sulfonium, etc.

The sulfonium salt of formula (1) can be synthesized by reacting a sulfoxide compound of the general formula (3) with trimethylsilyl-triflate and then with an aryl Grignard reagent of the general formula (4) prepared in an organic solvent such as tetrahydrofuran (THF), according to the following reaction scheme.

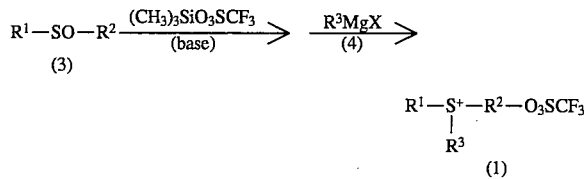

This reaction is preferably carried out in an organic solvent such as methylene chloride and THF. In the first stage of reacting a sulfoxide compound of formula (3) with trimethylsilyltriflate, trimethylsilyltriflate is added dropwise in an amount of about 1 to 2 mol per mol of the sulfoxide compound of formula (3). Where $R^1$ or $R^2$ in the sulfoxide compound of formula (3) has acid labile groups, reaction is desirably carried out in the presence of a base such as triethylamine and pyridine. Preferred reaction conditions include a temperature of about −78° C. to about 0° C. and a time of about 10 to 60 minutes.

In the second stage of reacting the intermediate with an aryl Grignard reagent of formula (4) prepared in an organic solvent such as THF, the aryl Grignard reagent is added dropwise in an amount of about 1 to 3 mol per mol of the sulfoxide compound of formula (3) at a temperature of about −78° C. to about 0° C. The reaction solution is preferably aged at a temperature of about 0° to 40° C. for about ½ to 2 hours. At the end of reaction, the solvent layer is washed with water and concentrated. The end sulfonium salt of formula (1) can be recovered by recrystallization or column fractionation.

A chemically amplified, positive working resist composition is also contemplated herein. The composition contains a sulfonium salt of formula (1). The sulfonium salt serves as a photo-acid-generator or as an additional component of a two component chemically amplified, positive resist composition consisting essentially of an alkali soluble resin and a photo-acid-generator or a three component chemically amplified, positive resist composition consisting essentially of an alkali soluble resin, a photo-acid-generator and a dissolution inhibitor. Preferably the sulfonium salt is added to a three component chemically amplified, positive resist composition.

Preferably the resist composition is comprised of, in parts by weight, (A) 150 to 700 parts, more preferably 250 to 500 parts of an organic solvent, (B) 70 to 90 parts, more preferably 75 to 85 parts of an alkali soluble resin, (C) 0 to 40 parts, more preferably 10 to 25 parts of a dissolution inhibitor having acid labile groups, (D) 0.1 to 5 parts, more preferably 0.8 to 4 parts of a sulfonium salt of formula (1), and (E) 0 to 15 parts, more preferably 2 to 8 parts of a photo-acid-generator.

Examples of organic solvent (A) include ketones such as cyclohexanone and methyl 2-n-amyl ketone; alcohols such as 3-methoxybutanol, 3-methyl-3-methoxybutanol, 1-methoxy-2-propanol and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate and ethyl 3-ethoxypropionate, alone or in admixture of two or more. The most preferred solvent is 1-ethoxy-2-propanol because the photo-acid-generator of the resist composition is most soluble therein.

Examples of alkali soluble resin (B) include polyhydroxystyrene and derivatives thereof. Preferred are those polyhydroxystyrene derivatives wherein some OH groups of polyhydroxystyrene are replaced by acid unstable groups. Examples of the acid labile group used herein include tert-butyl, tert-butoxy-carbonyl and tetrahydropyranyl groups. A degree of substitution of about 10 to 50 mol % and a weight average molecular weight of 5,000 to 100,000 are preferred.

Dissolution inhibitor (C) should have at least one group which is decomposable with an acid (acid labile group) in a molecule and may be either a low molecular weight compound or a polymer. Any of well-known dissolution inhibitors may be used. Exemplary low molecular weight compounds include bisphenol A derivatives having acid labile groups and carbonate derivatives having acid labile groups, with those bisphenol A derivatives wherein OH groups of bisphenol A are replaced by t-butoxy or butoxycarbonyloxy groups being preferred. Examples of the polymeric dissolution inhibitor include copolymers of p-butoxystyrene and t-butyl acrylate, and copolymers of p-butoxystyrene and maleic anhydride, with those copolymers having a weight average molecular weight of 500 to 10,000 being preferred.

Examples of photo-acid-generator (E) include onium salts, oxime sulfonic acid derivatives, 2,6-dinitrobenzylsulfonic acid derivatives, diazonaphthoquinone sulfonate derivatives, 2,4-bistrichloromethyl- 6-aryl- 1,3,5-triazine derivatives, and α,α'-bisarylsulfonyl diazomethane derivatives. Preferred are onium salts of the following general formula (2):

$$(R)_n MY \qquad (2)$$

wherein R is independently selected from substituted or unsubstituted aromatic groups, for example, phenyl, tert-butoxycarbonyloxy-phenyl, tert-butoxyphenyl, tert-butylphenyl, methoxyphenyl, and hydroxyphenyl groups; M is sulfonium or iodonium; Y is p-toluenesulfonate or trifluoromethanesulfonate; and letter n is equal to 2 or 3.

Illustrative examples of the onium salt are given by the following iodonium and sulfonium salts.

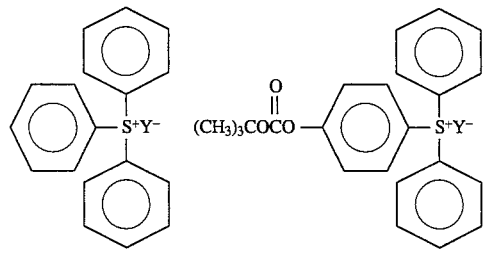

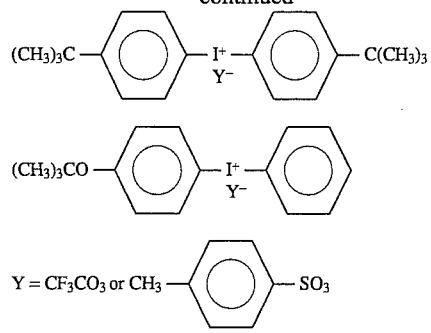

The resist composition of the invention may further contain a surfactant for improving coating properties and a light absorbing substance for reducing the influence of irregular reflection from the substrate.

With respect to the use of the resist composition of the invention and light exposure, any of well-known lithography techniques may be used. The resist composition of the invention is best suited for fine patterning using deep UV light of 254 to 193 nm and electron beams.

There has been described a resist composition which is sensitive to high energy rays, especially KrF excimer laser beams as a positive resist material and has high sensitivity, resolution and resistance to plasma etching with the resulting resist pattern having improved heat resistance. It is a chemically amplified, positive resist composition which has overcome the problem of an insoluble surface layer causing a T-top configuration, that is, the PED problem and which is suited for a fine patterning technique. The novel sulfonium salt of the invention is a useful component of such a chemically amplified, positive resist composition.

EXAMPLE

Examples of the present invention are given below by way of illustration and not by way of limitation.

Synthesis Example 1

Synthesis of trifluoromethanesulfonic acid bis(p-tert-butoxyphenyl)(p-dimethylamino-phenyl)sulfonium A solution of 8.5 g (0,025 mol) of bis(p-tert-butoxyphenyl)sulfoxide and 1.3 g (0.013 mol) of triethylamine in 110 g of methylene chloride was cooled to −70° C. with a dry ice methanol bath with stirring, 6.0 g (0,027 mol) of trimethylsilyltriflate was added dropwise to the solution while controlling the temperature so as not to exceed −60° C.

Thereafter, the dry ice methanol bath was replaced by an ice water bath whereupon the reaction solution was stirred for 10 minutes at a reaction temperature of 0° to 5° C.

The reaction solution was cooled again to −70° C. with a dry ice methanol bath. A Grignard reagent which was prepared from 1.2 g (0.049 mol) of metallic magnesium, 18.9 g of tetrahydrofuran and 9.9 g (0.049 mol) of 4-bromo-N,N-dimethylaniline in a conventional manner was added dropwise to the solution while controlling the temperature so as not to exceed −60°.

Thereafter, the dry ice methanol bath was replaced by an ice water bath whereupon the reaction solution was stirred for a further 60 minutes at a reaction temperature of 0° to 5° C., completing the solution.

Water was added dropwise to the reaction solution to decompose the excess of Grignard reagent and the resulting inorganic salt was removed by filtration. The filtrate was washed three times with 130 g of water. The organic layer was evaporated to dryness in vacuo, obtaining an oily product. The oily product was worked up by silica gel column chromatography, isolating trifluoromethanesulfonic acid bis(p-tert-butoxyphenyl)(p-dimethylaminophenyl)-sulfonium in an amount of 4.8 g (yield 32%) and a purity of 98%.

The end product was analyzed by nuclear magnetic resonance (NMR) spectrometry, infrared (IR) spectrometry, and elemental analysis, with the results shown below.

Proton NMR: $CDCl_3$, δ (ppm)

| | | | |
|---|---|---|---|
| (a) | 1.38 | singlet | 18 H |
| (b) | 3.00 | singlet | 6 H |
| (c) | 6.76–6.79 | doublet | 2 H |
| (e) | 7.11–7.15 | doublet | 4 H |
| (d), (f) | 7.40–7.45 | multiplet | 6 H |

IR: ($cm^{-1}$) 3095, 3072, 2980 , 2935 , 2873, 2827, 1589, 1520, 1489, 1446, 1373, 1308, 1265, 1223, 1203, 1157, 1074, 1030, 991, 927, 892, 816

Elemental analysis (%) for $C_{29}H_{36}F_3NO_5$ Calcd.: C: 58.1 H: 6.0 N: 2.3 Found: C: 57.8 H: 6.3 N: 2.2

Reference Example

A Grignard reagent was prepared in a conventional manner using 24.3 g (1 mol) of metallic magnesium, 203.2 g (1.1 mol) of p-tert-butoxyphenyl chloride and 280 g of THF. The Grignard reagent was diluted with 500 g of THF and cooled below −60° C. with a dry ice methanol bath. To the Grignard reagent solution, a solution of 47.5 g (0.4 mol) of thionyl chloride diluted with 70 g of THF was added dropwise over one hour at a temperature not exceeding 0° C. Stirring was continued for one hour on the ice bath and 36 g of water was then added to decompose the excess of Grignard reagent. To the reaction solution were added 1000 g of methylene chloride, 400 g of saturated ammonium chloride aqueous solution and 300 g of water. After layer separation, the organic solvent layer was washed twice with 700 g of pure water. The organic solvent layer was dried over magnesium sulfate, filtered, and evaporated to dryness in vacuo. The resulting oily product was recrystallized, recovering 83 g (yield 60%) of the end product, bis(p-tert-butoxy-phenyl)sulfoxide as a white crystal having a purity of 96% and a melting point of 80°–82° C.

Spectral data:

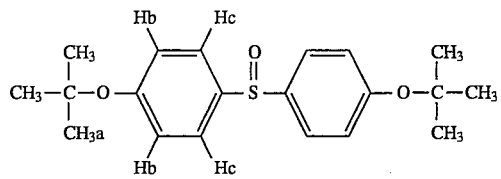

Proton NMR: $CDCl_3$, δ (ppm)

| | | | |
|---|---|---|---|
| 1.34 | Ha | singlet | 18H |
| 7.01–7.04 | Hb | doublet | 4H |
| 7.48–7.51 | Hc | doublet | 4H |

IR: ($cm^{-1}$) 2976, 2931, 1589, 1487, 1392, 1367, 1302, 1238, 1159, 1090, 1043 , 1009 , 930, 893 , 852 , 827

Elemental analysis (%) for $C_{20}H_{26}O_3S$ Calcd.: C: 69.3 H: 7.6 N: –Found: C: 69.6 H: 7.7 N: –

Mass spectrum (m/z) 346 ($M^+$): 331, 290 ($C_{20}H_{26}O_3S$= 346) mp: 80°–82° C.

Synthesis Example 2

Synthesis of trifluoromethanesulfonic acid (p-tert-butoxyphenyl)bis(p-dimethylamino-phenyl)sulfonium A solution of 7.0 g (0,024 mol) of bis(p-dimethylaminophenyl)sulfoxide in 100 g of methylene chloride was cooled to −70° C. with a dry ice methanol bath. With stirring, 6.0 g (0.027 mol) of trimethylsilyltriflate was added dropwise to the solution while controlling the temperature so as not to exceed −60° C.

Thereafter, the dry ice methanol bath was replaced by an ice water bath whereupon the reaction solution was stirred for 10 minutes at a reaction temperature of 0° to 5° C.

The reaction solution was cooled again to −70° C. with a dry ice methanol bath. A Grignard reagent which was prepared from 1.2 g (0.049 mol) of metallic magnesium, 13.4 g of tetra-hydrofuran and 9.8 g (0.053 mol) of p-tert-butoxyphenyl chloride in a conventional manner was added dropwise to the solution while controlling the temperature so as not to exceed −60° C.

Thereafter, the dry ice methanol bath was replaced by an ice water bath whereupon the reaction solution was stirred for a further 60 minutes at a reaction temperature of 0° to 5° C., completing the reaction.

Water was added dropwise to the reaction solution to decompose the excess of Grignard reagent and the resulting inorganic salt was removed by filtration. The filtrate was washed three times with 130 g of water. The organic layer was evaporated to dryness in vacuo, obtaining an oily product. The oily product was worked up by silica gel column chromatography, isolating trifluoromethanesulfonic acid (p-tert-butoxyphenyl)bis(p-dimethylamino-phenyl)sulfonium in an amount of 3.9 g (yield 28%) and a purity of 99%.

The end product was analyzed by nuclear magnetic resonance (NMR) spectrometry, infrared (IR) spectrometry, and elemental analysis, with the results shown below.

Proton NMR: CDCl₃, δ (ppm)

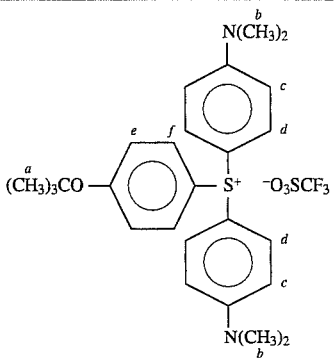

| (a) | 1.36 | singlet | 9 H |
|---|---|---|---|
| (b) | 2.99 | singlet | 12 H |
| (c) | 6.73–6.76 | doublet | 4 H |
| (e) | 7.08–7.11 | doublet | 2 H |
| (d), (f) | 7.29–7.34 | multiplet | 6 H |

IR: (cm$^{-1}$) 3097, 2978, 2929, 2908, 2870, 2825, 1589, 1551, 1518, 1487, 1446, 1373, 1265, 1223, 1200, 1155, 1074, 1030, 991, 943, 893, 816

Elemental analysis (%) for $C_{27}H_{33}F_3N_2O_4S_2$ Calcd.: C: 56.8 H: 5.8 N: 4.9 Found: C: 56.6 H: 6.1 N: 4.9

Synthesis Example 3

Synthesis of trifluoromethanesulfonic acid tris(4-dimethylaminophenyl)sulfonium

A solution of 7.0 g (0.024 mol) of bis(4-dimethylaminophenyl)sulfoxide in 100 g of methylene chloride was cooled to −70° C. with dry ice methanol bath. With stirring, 6.0g (0.027 mol) of trimethylsilyltriflate was added dropwise to the solution while controlling the temperature so as not to exceed −60° C.

Thereafter, the dry ice methanol bath was replaced by an ice water bath whereupon the reaction solution was stirred for 10 minutes at a reaction temperature of 0° to 5° C.

The reaction solution was cooled again to −70° C. with a dry ice methanol bath. A Grignard reagent which was prepared from 1.2 g (0.049 mol) of metallic magnesium, 20 g of tetra-hydrofuran and 9.9 g (0.049 mol) of 4-bromo-N,N-dimethylaniline in a conventional manner was added dropwise to the solution while controlling the temperature so as not to exceed −60° C.

Thereafter, the dry ice methanol bath was replaced by an ice water bath whereupon the reaction solution was stirred for a further 60 minutes at a reaction temperature of 0° to 5° C., completing the solution.

To the reaction solution was added 300 g of 15 wt % ammonium chloride aqueous solution to separate the organic phase from the aqueous phase. The organic phase was washed twice with 150 g of water. The solvent in the resulting organic phase was distilled off in vacuo by a rotary evaporator, obtaining an oily product. The oily product was worked up by silica gel column chromatography, isolating trifluoro-methanesulfonic acid tris(4-dimethylamino-phenyl)sulfonium in an amount of 5.2 g (yield 40%) and a purity of 99%.

The end product was analyzed by nuclear magnetic resonance (NMR) spectrometry, infrared (IR) spectrometry, and elemental analysis, with the results shown below.

Proton NMR: CDCl₃, δ (ppm)

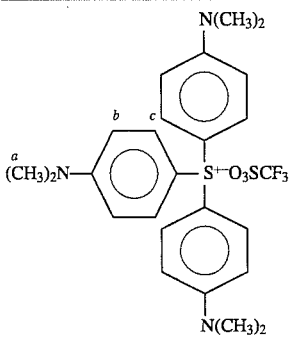

| (a) | 3.01 | singlet | 18 H |
|---|---|---|---|
| (b) | 6.72–6.75 | doublet | 6 H |
| (c) | 7.23–7.26 | doublet | 6 H |

IR: (cm$^{-1}$) 2910, 1591, 1550, 1515, 1444, 1375, 1272, 1222, 1199, 1145, 1076, 1031, 991, 943, 811, 638, 520

Elemental analysis (%) for $C_{25}H_{30}O_3N_3S_2F_3$ Calcd.: C: 55.4 H: 5.6 N: 7.8 Found: C: 55.3 H: 5.6 N: 7.7

Examples 1–11 & Comparative Examples 1–4

Liquid resist compositions were prepared by dissolving a polyhydroxystyrene derivative of the following formula Polym. 1 wherein some OH groups are protected by t-butoxycarbonyl groups, a polyhydroxystyrene derivative of the following formula Polym. 2 wherein some OH groups are protected by t-butyl groups, or a polyhydroxystyrene derivative of the following formula Polym. 3 wherein some OH groups are protected by tetrahydropyranyl groups, a photoacid-generator selected from the onium salts of the formulae PAG. 1 to PAG. 7, and a dissolution inhibitor in the form of 2,2'-bis-(4-tert-butoxycarbonyloxyphenyl)propane of the formula DRI. 1, in 1-ethoxy-2-propanol (EtOIA) in accordance with the formulation shown in Table 1.

Each of the compositions was passed through a 0.2 -μm Teflon® filter. It was then spin coated onto a silicon wafer to form a coating of 1.0 μm thick. With the silicon wafer rested on a hot plate at 100° C., the coating was pre-baked for 120 seconds.

The film was exposed to a pattern of light by means of an excimer laser stepper model NSR 2005EX (manufactured by Nikon K.K., numerical aperture NA=0.5), baked at 90° C. for 60 seconds, and developed with an aqueous solution of 2.38% tetramethylammonium hydroxide, obtaining a positive pattern.

The resulting resist pattern was evaluated as follows.

First, sensitivity (Eth value) was determined. Provided that the exposure quantity with which the top and bottom of a 0.4 -μm line-and-space pattern were resolved at 1:1 was the optimum exposure, the minimum line width of a line-and-space pattern which was recognized separate at this exposure was the resolution of a test resist. The configuration of the resist pattern resolved was observed under a scanning electron microscope. The resist was determined for PED stability by exposing at the optimum exposure, leaving the resist film to stand for a varying time, and baking the film. The leave-to-stand time was determined at which a change in the resist pattern configuration was observed, for example, the line pattern was T-top configured or resolution became impossible. The longer the leave-to-stand time, the better is the PED stability.

The results are shown in Table 1.

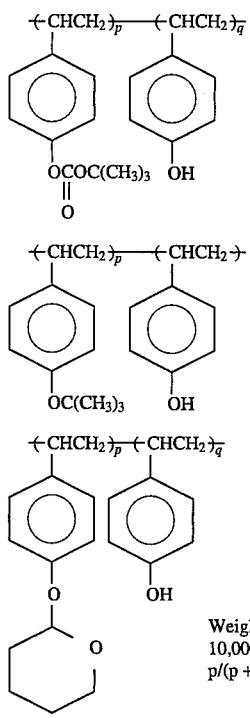  <Polym.>
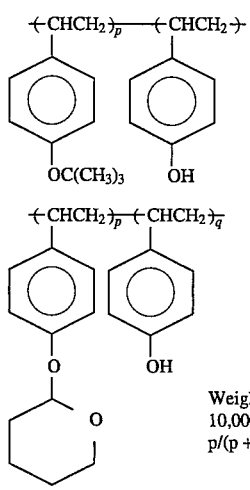  <Polym. 2>
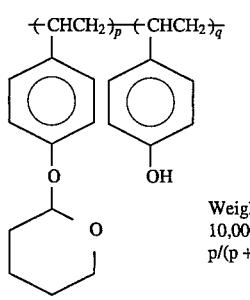  <Polym. 3>
Weight average molecular weight
10,000–50,000
$p/(p+q) = 0.1$–$0.3$
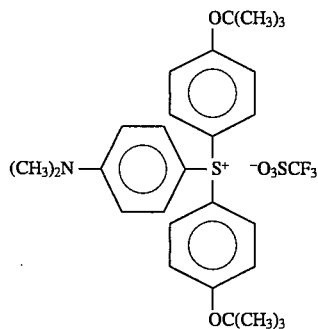  <PAG. 1>
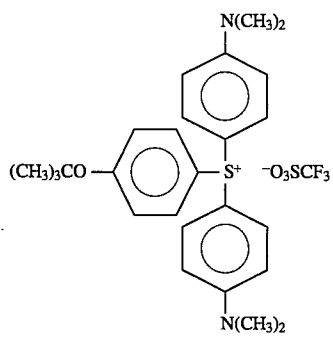  <PAG. 2>
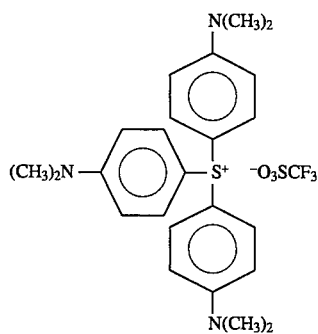  <PAG. 3>

-continued
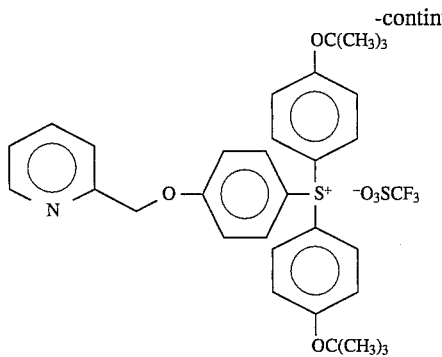
<PAG. 4>
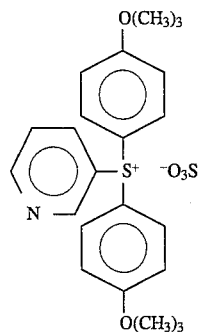
<PAG. 5>
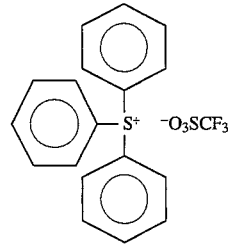
<PAG. 6>
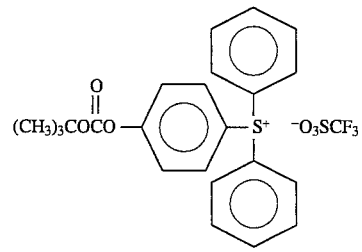
<PAG. 7>
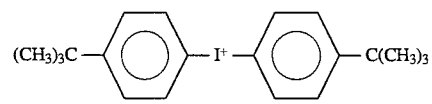
<PAG. 8>
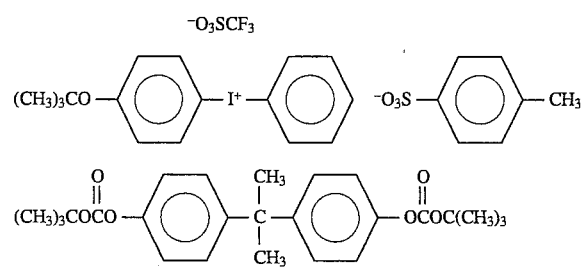
<PAG. 9>
<DRI. 1>

Note that PAG. 4 and PAG. 5 were synthesized as in Synthesis Examples 1 and 2.

TABLE 1

| Example | Resist composition (pbw) | | | | Sensitivity (mJ/cm$^2$) | Resolution (μm) | Pattern shape | PED stability (min.) |
|---|---|---|---|---|---|---|---|---|
| | Alkali soluble resin | Photo-acid-generator | Dissolution inhibitor | Solvent | | | | |
| E 1 | Polym.1(80) | PAG.1(3) | DRI.1(20) | EtOIPA(450) | 115.0 | 0.28 | good | ≧120 |
| E 2 | Polym.2(80) | PAG.2(3) | DRI.1(20) | EtOIPA(450) | 170.0 | 0.28 | good | ≧120 |
| E 3 | Polym.1(80) | PAG.3(3) | DRI.1(20) | EtOIPA(450) | 200.0 | 0.29 | good | ≧120 |
| E 4 | Polym.3(80) | PAG.4(3) | DRI.1(20) | EtOIPA(450) | 110.0 | 0.28 | good | ≧120 |
| E 5 | Polym.1(75) | PAG.1(1) PAG.6(4) | DRI.1(15) | EtOIPA(500) | 11.5 | 0.28 | good | ≧120 |
| E 6 | Polym.2(75) | PAG.1(1) PAG.7(4) | DRI.1(15) | EtOIPA(500) | 14.0 | 0.25 | good | ≧120 |
| E 7 | Polym.3(75) | PAG.2(0.5) PAG.8(3.5) | DRI.1(15) | EtOIPA(450) | 19.0 | 0.28 | good | 60 |
| E 8 | Polym.1(75) | PAG.2(0.5) PAG.7(3.5) | DRI.1(10) | EtOIPA(450) | 66.0 | 0.25 | good | 60 |
| E 9 | Polym.2(70) | PAG.4(1.5) PAG.6(3.5) | DRI.1(10) | EtOIPA(500) | 10.0 | 0.28 | good | ≧120 |
| E 10 | Polym.3(70) | PAG.5(1.5) PAG.6(3.5) | DRI.1(10) | EtOIPA(500) | 19.0 | 0.28 | good | ≧120 |
| E 11 | Polym.1(80) | PAG.5(1) PAG.6(4) | — | EtOIPA(400) | 15.0 | 0.30 | good | ≧120 |
| CE 1 | Polym.1(75) | PAG.6(5) | DRI.1(20) | EtOIPA(450) | 4.0 | 0.35 | somewhat T-topped | ≦5 |
| CE 2 | Polym.2(75) | PAG.7(5) | DRI.1(20) | EtOIPA(450) | 4.0 | 0.25 | good | 10 |
| CE 3 | Polym.3(75) | PAG.8(5) | DRI.1(20) | EtOIPA(450) | 4.0 | 0.30 | somewhat T-topped | ≦5 |
| CE 4 | Polym.1(80) | PAG.6(5) | — | EtOIPA(400) | 5.0 | 0.40 | good | ≦5 |

EtOIPA: 1-ethoxy-2-propanol

Japanese Patent Application No. 6-26170 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A sulfonium salt of the following general formula (1):

(1)

wherein $R^1$, $R^2$, and $R^3$ are each independently a substituted or unsubstituted aromatic group, at least one of $R^1$, $R^2$, and $R^3$ is a substituted aromatic group having an acid labile group, and at least one of the remaining R groups is a nitrogenous aromatic group, or all of $R^1$, $R^2$ and $R^3$ are nitrogenous aromatic groups.

2. A salt of claim 1, wherein the substituted aromatic group having an acid labile group is tert-butoxyphenyl, and the nitrogenous aromatic group is dialkylaminophenyl wherein the alkyl moieties each have 1 to 8 carbon atoms, picolyloxyphenyl or pyridinyl.

3. In a resist composition comprising a sulfonium salt, the improvement wherein said salt is one of claim 1.

4. A resist composition comprising (A) an organic solvent, (B) an alkali solution resin, optionally (C) a dissolution inhibitor having acid labile groups, (D) a sulfonium salt set forth in claim 1, and optionally (E) a photo-acid generator.

5. A composition of claim 4, wherein said alkali soluble resin (B) is a polyhydroxystyrene in which hydrogen atoms of some hydroxyl groups are replaced by acid labile groups, and said polyhydroxystyrene has a weight average molecular weight of 5,000 to 100,000.

6. A resist composition according to claim 4, wherein said composition comprises (E) a photo-acid-generator.

7. A resist composition according to claim 4, wherein said composition comprises (C) a dissolution inhibitor having acid labile groups.

8. A resist composition according to claim 6, wherein said composition comprises (C) a dissolution inhibitor having acid labile groups.

9. A resist composition of claim 3, wherein the substituted aromatic group having an acid labile group is tert-butoxyphenyl, and the nitrogenous aromatic group is dialkylaminophenyl wherein the alkyl moieties have 1 to 8 carbon atoms, picolyloxyphenyl or pyridinyl.

10. A resist composition of claim 4, wherein the substituted aromatic group having an acid labile group is tert-butoxyphenyl, and the nitrogenous aromatic group is dialkylaminophenyl wherein the alkyl moieties have 1 to 8 carbon atoms, picolyloxyphenyl or pyridinyl.

11. A resist composition of claim 6, wherein the substituted aromatic group having an acid labile group is tert-butoxyphenyl, and the nitrogenous aromatic group is dialkylaminophenyl wherein the alkyl moieties have 1 to 8 carbon atoms, picolyloxyphenyl or pyridinyl.

12. A composition of claim 6, wherein said alkali soluble resin (B) is a polyhydroxystyrene in which hydrogen atoms of some hydroxyl groups are replaced by acid labile groups, and said polyhydroxystyrene has a weight average molecular weight of 5,000 to 100,000.

13. A salt according to claim 1, wherein at least one of $R^1$, $R^2$ and $R^3$ is picolyloxyphenyl, pyridinyl or dialkylaminophenyl wherein the alkyl moieties in each case have 1–8 C atoms.

14. A salt according to claim 13, wherein at least one of $R^1$, $R^2$ and $R^3$ is dimethylaminophenyl, diethylaminophenyl, picolyloxyphenyl or pyridinyl.

15. A salt according to claim 1, wherein at least one of $R^1$, $R^2$ and $R^3$ is tert-butoxyphenyl.

16. A salt according to claim 14, wherein at least one of $R^1$, $R^2$ and $R^3$ is tert-butoxyphenyl.

17. A salt according to claim 1, wherein said salt is:

trifluoromethanesulfonic acid bis(p-tert-butoxyphenyl)(p-dimethylaminophenyl)sulfonium, trifluoromethanesulfonic acid (p-tert-butoxyphenyl)-bis(p-dimethylaminophenyl)sulfonium, trifluoromethanesulfonic acid bis (p-tert-butoxyphenyl)(p-picolyloxyphenyl)sulfonium, trifluoromethanesulfonic acid (p-tert-butoxyphenyl)bis(p-picolyloxyphenyl)sulfonium, trifluoromethanesulfonic acid (p-tert-butoxyphenyl)(p-dimethylaminophenyl)phenylsulfonium, trifluoromethanesulfonic acid (p-tert-butoxyphenyl)(p-picolyloxyphenyl)phenylsulfonium, trifluoromethanesulfonic acid bis(p-tert-butoxyphenyl)(pyridin-4-yl)sulfonium, trifluoromethanesulfonic acid bis (p-tert-butoxyphenyl)(pyridin-3-yl)sulfonium, trifluoromethanesulfonic acid bis (p-tert-butoxyphenyl)(pyridin-2-yl)sulfonium or trifluoromethanesulfonic acid tris (4-dimethylaminophenyl)sulfonium.

18. A salt according to claim 1, wherein $R^1$, $R^2$ and $R^3$ are each independently phenyl, tert-butoxyphenyl, picolyloxyphenyl, pyridinyl or dialkylaminophenyl wherein the alkyl moieties in each case have 1–8 C atoms, at least one of $R^1$, $R^2$ and $R^3$ is tert-butoxyphenyl, and at least one of the remaining R groups is dialkylaminophenyl wherein the alkyl moieties in each case have 1–8 C atoms, picolyloxyphenyl or pyridinyl, or all of $R^1$, $R^2$ and $R^3$ are each dialkylaminophenyl wherein the alkyl moieties have 1–8 C atoms, picolyloxyphenyl or pyridinyl.

19. A resist composition according to claim 4, wherein said composition contains 150–700 parts by weight of organic solvent (A), 70–90 parts by weight of alkali soluble resin (B), 0–40 parts by weight dissolution inhibitor (C), 0.1–5 parts by weight sulfonium salt (D) and 0–15 parts by weight photo-acid-generator (E).

20. A resist composition according to claim 19, wherein said composition contains 250–500 parts by weight of organic solvent (A), 75–85 parts by weight of alkali soluble resin (B), 10–75 parts by weight of dissolution inhibitor (C), 0.8–4 parts by weight of sulfonium salt (D) and 2–8 parts by weight of photo-acid-generator (E).

21. A resist composition according to claim 4, wherein said alkali soluble resin (B) is a polyhydroxystyrene wherein some but not all of the OH groups are protected by acid labile groups selected from tert-butyl, tert-butoxy-carbonyl and tetrahydropyranyl.

22. A resist composition according to claim 21, wherein the amount of hydroxy groups in said polyhydroxystyrene that are protected by tert-butyl, tert-butoxy-carbonyl and/or tetrahydropyranyl is 10–15 mole % and the weight average molecular weight of said polyhydroxystyrene is 5,000–100,000.

23. A resist composition according to claim 6, wherein said photo-acid-generator (E) is an onium salt of the formula (2):

$$(R)_n MY \qquad (2)$$

wherein

R is phenyl, tert-butoxycarbonyloxyphenyl, tert-butoxyphenyl, tert-butylphenyl, methoxyphenyl or hydroxyphenyl;

M is sulfonium or iodonium;

Y is p-toluenesulfonate or trifluoromethanesulfonate; and n is 2 or 3.

24. A resist composition according to claim 4, further comprising a surfactant and/or a light-absorbing substance.

* * * * *